(12) United States Patent
Lee et al.

(10) Patent No.: US 8,584,046 B2
(45) Date of Patent: Nov. 12, 2013

(54) VISUALIZING DIFFERENCES IN SIMILARITY METRICS OF HIERARCHIES

(75) Inventors: Bongshin Lee, Issaquah, WA (US); George G. Robertson, Seattle, WA (US)

(73) Assignee: Microsoft Corporation, Redmond, WA (US)

(*) Notice: Subject to any disclaimer, the term of this patent is extended or adjusted under 35 U.S.C. 154(b) by 1313 days.

(21) Appl. No.: 11/733,036

(22) Filed: Apr. 9, 2007

(65) Prior Publication Data
US 2008/0250357 A1 Oct. 9, 2008

(51) Int. Cl.
| G06F 3/048 | (2013.01) |
| G06F 17/30 | (2006.01) |
| G06F 3/0481 | (2013.01) |
| G06F 3/0484 | (2013.01) |
| G06F 19/14 | (2011.01) |

(52) U.S. Cl.
CPC ........ *G06F 3/0481* (2013.01); *G06F 17/30572* (2013.01); *G06F 17/30961* (2013.01); *G06F 17/30126* (2013.01); *G06F 3/04842* (2013.01); *G06F 2203/04804* (2013.01); *G06F 19/14* (2013.01)
USPC .......................................... 715/854; 707/797

(58) Field of Classification Search
USPC ................................................ 715/853–854
See application file for complete search history.

(56) References Cited

U.S. PATENT DOCUMENTS

| 6,219,833 | B1 * | 4/2001 | Solomon et al. | 717/149 |
| 6,496,208 | B1 * | 12/2002 | Bernhardt et al. | 715/853 |
| 6,628,313 | B1 * | 9/2003 | Minakuchi et al. | 715/853 |
| 2004/0230952 | A1 * | 11/2004 | Massaro et al. | 717/120 |
| 2006/0136193 | A1 * | 6/2006 | Lux-Pogodalla et al. | 704/2 |
| 2006/0161869 | A1 * | 7/2006 | Robertson et al. | 715/853 |
| 2007/0150443 | A1 * | 6/2007 | Bergholz et al. | 707/3 |

OTHER PUBLICATIONS

Gordon, A. D. Consensus supertrees: The synthesis of rooted trees containing overlapping sets of labeled leaves. Journal of Classification 3, 335-348 (1986).*
Morse, D. R., Ytow, N., Roberts, D. M. & Sato, A. Comparison of multiple taxonomic hierarchies using TaxoNote. In Infovis 2003 (IEEE, 2003). 5 pages.*
Graham, M. & Kennedy, J. A survey of multiple tree visualisation. Information Visualization 9, 235-252 (2009).*
Parr, C. S., Lee, B., Campbell, D. & Bederson, B. B. Visualizations for taxonomic and phylogenetic trees. Bioinformatics 20, 2997-3004 (2004).*
Robertson, G. G., Czerwinski, M. P. & Churchill, J. E. Visualization of mappings between schemas. SIGCHI Conference on Human Factors in Computing Systems 431-439 (2005).*

(Continued)

*Primary Examiner* — Soren Harward

(57) ABSTRACT

A hierarchy differences visualization system and method for visualizing differences between two hierarchical structures based on similarity metrics. The two hierarchical structures are merged into a merged hierarchical structure and differences between the two hierarchical structures are computed and displayed in a user interface using node visualization metrics. In addition, at least one path is computed to a root of the merged hierarchical structure from a selected node and displayed in the user interface. The user interface uses various node visualization metrics including color, shapes, size, underlining, strikethrough, and text transparency. In some embodiments the hierarchical structures are tree structures and the similarity metric is structural uncertainty including location uncertainty and sub-tree structure uncertainty. The location uncertainty of a node is indicated by a color of the node label and sub-tree structure uncertainty of a node is shown by various levels of transparency of node labels.

20 Claims, 8 Drawing Sheets

(56) References Cited

OTHER PUBLICATIONS

Bederson, B. B., J. Grosjean, J. Meyer, Toolkit design for interactive structured graphics, IEEE Trans. on Software Eng'g, Aug. 2004, pp. 535-546, vol. 30, No. 8.
Eaton, C., C. Plaisant, and T. Drizd, Visualizing missing data: Graph interpretation user study, Human-Computer Interaction—Interact, 2005, pp. 861-872.
Fegeas R. G., J. L. Cascio, R. A. Lazar, An overview of FIPS 173, The spatial data transfer standard, Cartography and Geographic Information Systems, 1992, vol. 19, No. 5, pp. 278-293.
Furnas, G. W., Generalized fisheye views, Human Factors in Computing Systems CHI '86 Conf. Proc., 1986, pp. 16-23.
Gershon, N. D., Visualization of fuzzy data using generalized animation, Proc. of the 3rd Conf. on Visualization, 1992, pp. 268-273.
Griethe, H., and H. Schumann, The visualizations of uncertain data: Methods and problems, Proc. of SimVis 2006, pp. 143-156.
Hong, J.Y., J. D'Andries, M. Richman, and M. Westfall, Zoomology: Comparing two large hierarchical trees, Proc. Poster Compendium of the IEEE Symposium of Info. Visualization, 2003, pp. 120-121.
Lee, B., C. S. Parr, D. Campbell, B. B. Bederson, How users interact with biodiversity information using TaxonTree, Proc. of the Working Conf. on Advanced Visual Interfaces, 2004, pp. 320-327.
Lodha, S. K., C. M. Wilson, R. E. Sheehan, LISTEN: Sounding uncertainty visualization Visualization Proceedings, Oct. 27-Nov. 1, 1996, pp. 189-195.
Lodha, S. K., A. Pang, R. E. Sheehan, and C. M. Wittenbrink, UFLOW: Visualizing uncertainty in fluid flow, IEEE Visualization '96, 1996, pp. 249-254.
MacEachren, A. M., A. Robinson, S. Hopper, S. Gardner, R. Murray, & M. Gahegan, Visualizing geospatial information uncertainty: What we know and what we need to know, Cartographic and Geographic Information Science, 2005, pp. 139-160, vol. 32, No. 3.
Morse, D. R., N. Ytow, D. M. Roberts and A. Sato, Comparison of multiple taxonomic hierarchies using TaxoNote, IEEE Symposium on Info. Visualisation, Seattle, Oct. 19-21, 2003.
Munzner, T., F. Guimbretiere, S. Tasiran, L. Zhang, and Y. Zhou, TreeJuxtaposer: Scalable tree comparison using focus+context with guaranteed visibility, ACM Trans. on Graphics, vol. 22, No. 3, pp. 453-462, 2003.
Nye, T. M., P. Li, W. R. Gilks, A novel algorithm and web-based tool for comparing two alternative phylogenetic trees, Bioinformatics, Jan. 1, 2006, pp. 117-119, vol. 22, No. 1.
Olston, C., and J. Mackinlay, Visualizing data with bounded uncertainty, Technical report, Stanford University Computer Science Department, 2002.
Pang, A. Visualizing uncertainty in geo-spatial data, Workshop on the Intersections between Geospatial Information and Information Technology, prepared for the National Academies committee of the Computer Science and Telecomm Unifications Board, 2001.
Pang, A., and A. Freeman, Methods for comparing 3D surface attributes, SPIE vol. 2656, Visual Data Exploration and Analysis III, Feb. 1996, pp. 58-64.
Pang, A. T., C. M. Wittenbrink, and S. K. Lodha, Approaches to uncertainty visualization, The Visual Computer, 1997, pp. 370-390, vol. 13, No. 8.
Spenke, M., and C. Beilken, Visualization of trees as highly compressed tables with InfoZoom, IEEE Symposium on Information Visualization, 2003, pp. 122-123.
Sulo, R., S. Eick, R. Grossman, DaVis: A tool for visualizing data quality, submitted for publication, InfoViz 2005.
Taylor, B. N., and C. E. Kuyatt, Guidelines for evaluating and expressing the uncertainty of NIST measurement results, Technical report, National Institute of Standards and Technology, Note 1297, Gaithersburg, Maryland, 1994.
Thomson, J., B. Hetzler, A. MacEachren, M. Gahegan, and M. Pavel, A typology for visualizing uncertainty, Conference on Visualization and Data Analysis, Jan. 16-20, 2005, San Jose, CA USA (2005).
Walker, J.Q., A node-positioning algorithm for general trees, Software—Practice and Experience, 1990, pp. 685-705, vol. 20, No. 7.
Wittenbrink, C. M., A. T. Pang, S. K. Lodha, Glyphs for Visualizing Uncertainty in Vector Fields, IEEE Transactions on Visualization and Computer Graphics, Sep. 1996, pp. 266-279, vol. 2, No. 3.
Piccolo, A Structured 2D Graphics Framework, retrieved Nov. 2006 from http://www.cs.umd.edu/hcil/piccolo/.
Hyperbolic tree for the Green Tree of Life, retrieved Feb. 2007 from http://ucjeps.berkeley.edu/TreeofLife/hyperbolic.php/.
Lee, B., et al. "CandidTree: Visualizing Structural Uncertainty in Similar Hierarchies"; Information Visualization; vol. 6, No. 3; 2007; pp. 233-246.
Levenshtein, "Binary Codes Capable of Correcting Deletions, Insertions, and Reversals", Soviet Physics-Doklady, Feb. 1966.

* cited by examiner

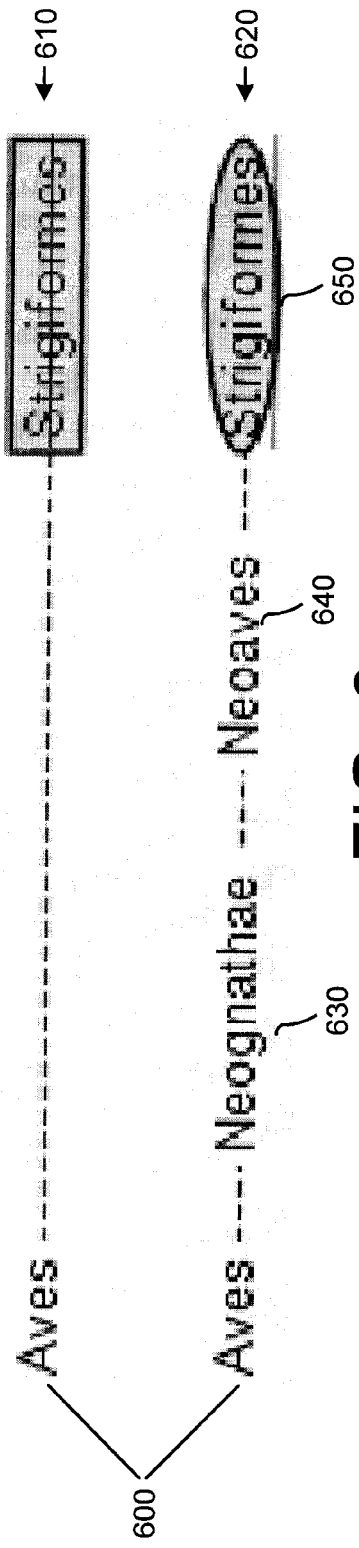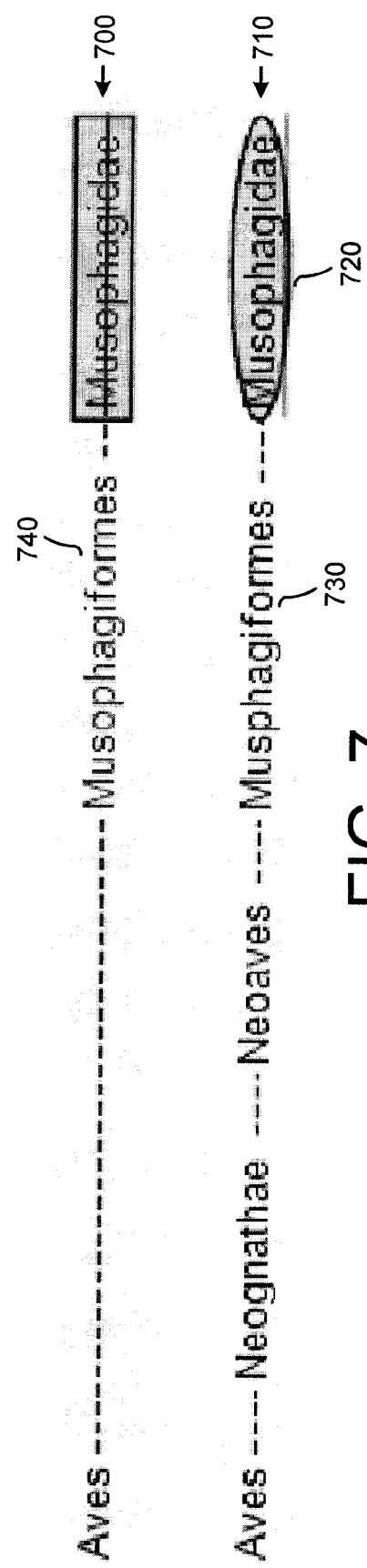
FIG. 6
FIG. 7

VISUALIZING DIFFERENCES IN SIMILARITY METRICS OF HIERARCHIES

BACKGROUND

Most current visualization systems generally suggest certainty. This means that when visualizations are displayed to users, they believe that what is currently displayed is absolute truth. However, there are many cases where this is not true. For example, several biological taxonomies and phylogenetic trees exist because not all biologists agree on one taxonomy or one phylogenetic tree and some analysis methods produce multiple possible trees. Some existing tree visualizations typically show one taxonomy at a time without any certainty information. Hence, there is no way to see which parts of the tree are certain or uncertain.

One common approach to comparing two tree structures is to use paired views side-by-side, using coupled interaction to allow users to compare and navigate two trees. This approach helps users identify where the differences are in two trees (usually by highlighting). However, this approach does not explicitly show the degree to which two parts are different.

To provide a complete and accurate visual representation of data, it is important to show uncertainty within the data. Uncertainty has been very broadly defined to include concepts such as error, inaccuracy/imprecision, minimum-maximum ranges, data quality, and missing data. For more than a decade, much research has described approaches to handling these various aspects of uncertainties. Geographic Visualization, Geographic Information System, and Scientific Visualization communities have given particular attention to uncertainty visualization and many techniques have been developed. The main techniques used to visualize uncertainty include adding glyphs, adding geometry, modifying geometry, modifying attributes, animation, sonification, and psycho-visual approach. While these techniques have been applied to a variety of applications such as fluid flow, surface interpolants, and volumetric rendering, only a few of them were actually evaluated. Furthermore, there has been little research on visualizing uncertainty in tree structures. One such study proposed visual representations to represent uncertainty in parent-child relationship in structures. For example, for node-link diagrams this study used blurred or dotted links to indicate less certain relationships. However, this study did not describe how to represent the degree of uncertainty.

An error can be defined as a difference between a computed, estimated, or measured value and the true or correct value. There are many cases where correct values are unknown but can be estimated using different techniques or algorithms. It is common to use the differences between two results as an error (or uncertainty). In fact, side-by-side comparison is one of the most commonly applied existing uncertainty visualization methods. Therefore, theoretically these kinds of visualization tools can be used to show uncertainty in tree structures.

In the biology domain, there exist several biological taxonomies and phylogenetic trees because not all biologists agree on one taxonomy and one phylogenetic tree. In order to assess the quality of taxonomies and phylogenetic trees, it is important to understand which parts of two trees agree or disagree. One of the commonly used approaches to comparing two trees is to use paired views side-by-side, using coupled interaction. For example, one approach automatically matches nodes in two trees based on the shared ancestors, and highlights the differences locations. Another approach transforms a tree into a tabular representation, in which each leaf is represented as a column and the path from the root is stored in the attributes (rows). It displays both trees (in a tabular form) side-by-side and marks the cells of differences. Some visualizations provide a merged tree by combining two trees into one. One such visualization shows the merged tree on left, first tree at center, and second tree on right. It uses multiple tables to provide taxonomic names that are common or different. Another visualization also provides a single overview of the merged tree with the indication of difference, and uses matched twin detail windows to show similarities and differences via a zoomable interface. However, while these tools show the location of the differences, they fail to show the magnitude of the differences.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The hierarchy differences visualization system and method disclosed herein merges two hierarchical structures into a single hierarchical structure and computes differences between the two hierarchical structures based on similarity metrics. The two hierarchical structures are merged into a single merged hierarchical structure. The merged hierarchical structure is displayed to a user along with the differences using a node visualization metric. In addition at least one path is computed to a root of the merged hierarchical structure from a selected node.

In some embodiments the hierarchical structures are tree structures. By way of example, these tree structures can be used to represent backup file directory structures (for two different time points) containing backups for the same folder. The system and method can be used to help users find added, deleted, or moved files, in addition to modified folders. Moreover, the system and method enable a user to identify which folder has been changed the most or least. Another example is tree structures of two classifications of scientific names. Sometimes differences exist between the two classifications, and these differences can be visualized by the hierarchy differences visualization system and method.

In other embodiments the similarity metric is structural uncertainty. Structural uncertainty is defined as the differences between two tree structures. The hierarchy differences visualization system and method compute two types of structural uncertainty: (1) location uncertainty (which is the location of a node relative to its parent); and, (2) sub-tree structure uncertainty of a node. Three possible degrees of location uncertainty exist, and each is visualized on the merged tree structure. The sub-tree structure uncertainty is computed by measuring how many links overlap in two sub-tree structures. A sub-tree structure function defined for a node is used in the computation of sub-tree structure uncertainty.

A hierarchical differences user interface is used to display the merged hierarchical structure, the differences in the similarity metrics, and the node visualization metrics. The user interface includes a tree browser area, for displaying the merged hierarchical structure, and a paths view area for displaying path computed for nodes on the structure. The user interface also includes a certainty range bar that allows a user to unhighlight nodes that do not meet a certainty requirement. This feature helps a user focus on the nodes with a specific certainty range and filter out nodes that do not meet the certainty requirement. Moreover, the user interface includes a search feature that allows a user to type in a search term and obtains search results. For example, a user can search the merged hierarchical structure for a term and obtain search results such that only nodes relevant to the search results are displayed.

The user interface also includes node visualization metrics displayed on the merged hierarchical structure. Various node visualization metrics are used in different embodiments. For example, in some embodiments, the location uncertainty of a node relative to its parent is indicated by a color of the node label. In other embodiments, a first color is used to indicate a node has been deleted and a second color indicates that a node has been added. Strikethrough and underlining are used to indicate that the node was moved from one location to another. In yet other embodiments, sub-tree structure uncertainty of a node is shown by various levels of transparency of node labels. Thus, the more certain the data (and the less uncertainty) the more opaque (and readable) are the node labels. The user interface also includes a "Highlight Changes" check box that reverses the levels of transparency as desired by a user. The user interface also allows a user to interactively explore the merged tree structure to further investigate parts of the structure.

The hierarchy differences visualization system and method can also be used to visualize more than two tree structures by providing the list of every possible combination of those tree structures and showing only one combination at once. By ranking each combination based on the structural uncertainty, the user can easily identify most certain/uncertain (similar/dissimilar) tree structure combinations. Moreover, the system and method loads entire tree structures and builds the merged tree structure in memory. Because this is impractical with large tree structures, the generating of the merged tree structure and accompanying structural uncertainty computations may be stored in a database. By accessing the data from a database when needed, the hierarchy differences visualization system and method can be scaled up to support very large trees and with multiple attributes.

It should be noted that alternative embodiments are possible, and that steps and elements discussed herein may be changed, added, or eliminated, depending on the particular embodiment. These alternative embodiments include alternative steps and alternative elements that may be used, and structural changes that may be made, without departing from the scope of the invention.

DRAWINGS DESCRIPTION

Referring now to the drawings in which like reference numbers represent corresponding parts throughout:

FIG. 6 is an example illustrating of visualizing the path computation of two paths to a root in a first tree structure and a second tree structure.

FIG. 7 is an example of node alignment with similar labels from two paths.

DETAILED DESCRIPTION

In the following description of the hierarchical shared resources spatial visualization system and method, reference is made to the accompanying drawings, which form a part thereof, and in which is shown by way of illustration a specific example whereby the hierarchical shared resources spatial visualization system and method may be practiced. It is to be understood that other embodiments may be utilized and structural changes may be made without departing from the scope of the claimed subject matter.

I. General Overview

Figure 1:
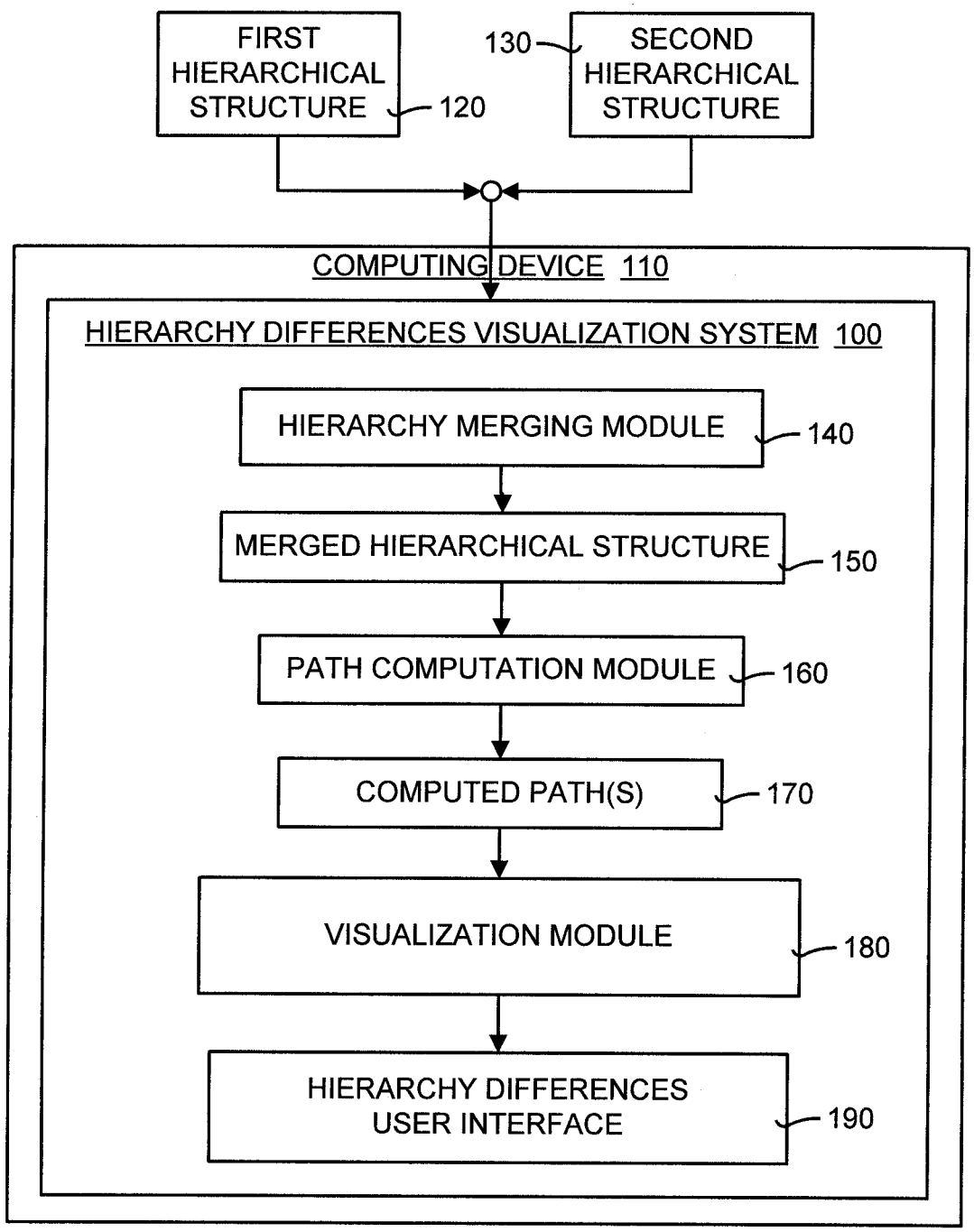
FIG. 1 is a block diagram illustrating the general overview of the hierarchy differences visualization system and method.

FIG. 1 is a block diagram illustrating the general overview of the hierarchy differences visualization system and method. In particular, the hierarchy differences visualization system 100 operates in a computing environment on a computing device 110. As described below, this computing device 110 can be any type of device utilizing a processor.

The hierarchy differences visualization system 100 inputs a first hierarchical structure 120 and a second hierarchical structure 130 for processing and examination. Although FIG. 1 illustrates that the structures 120, 130 are outside the computing device 110, it should be noted that the structures 120, 130 may be created or otherwise obtained from the computing device 110 itself. Moreover, the structures 120, 130 may be changing in time. The first hierarchical structure 120 and the second hierarchical structure 130 can also be called tree structures. In general, a hierarchy is a system of ranking and organizing items, whereby each element of the system (except for the top element) is subordinate to a single other element. More specifically, the technical definition for a hierarchy or tree structure is a connected acyclic graph. "Tree" is a technical term while "hierarchy" is a common language term for the same thing.

The hierarchy differences visualization system 100 includes a hierarchy merging module 140 that merges the first hierarchical structure 120 and the second hierarchical structure 130 to generate a merged hierarchical structure 150. Thus, the merged hierarchical structure 150 represents the merging of the first and second hierarchical structures 120, 130. The hierarchy differences visualization system 100 also includes a path computation module 160 that analyzes the merged hierarchical structure 150 and generates a computed path or paths 170. As set forth in detail below, the determination of whether the path computation module 160 computes a single path or two paths depends mainly on the choice of node in the merged hierarchical structure 150.

The hierarchy differences visualization system 100 also includes a visualization module 180 that provides the information computed above to generate and populate a hierarchy differences user interface 190. As discussed in detail below, the user interface 190 contains several pieces of information that allow a user to quickly and efficiently observe and interpret differences between similarity metrics in the first hierarchical structure 120 and the second hierarchical structure 130.

Figure 2:
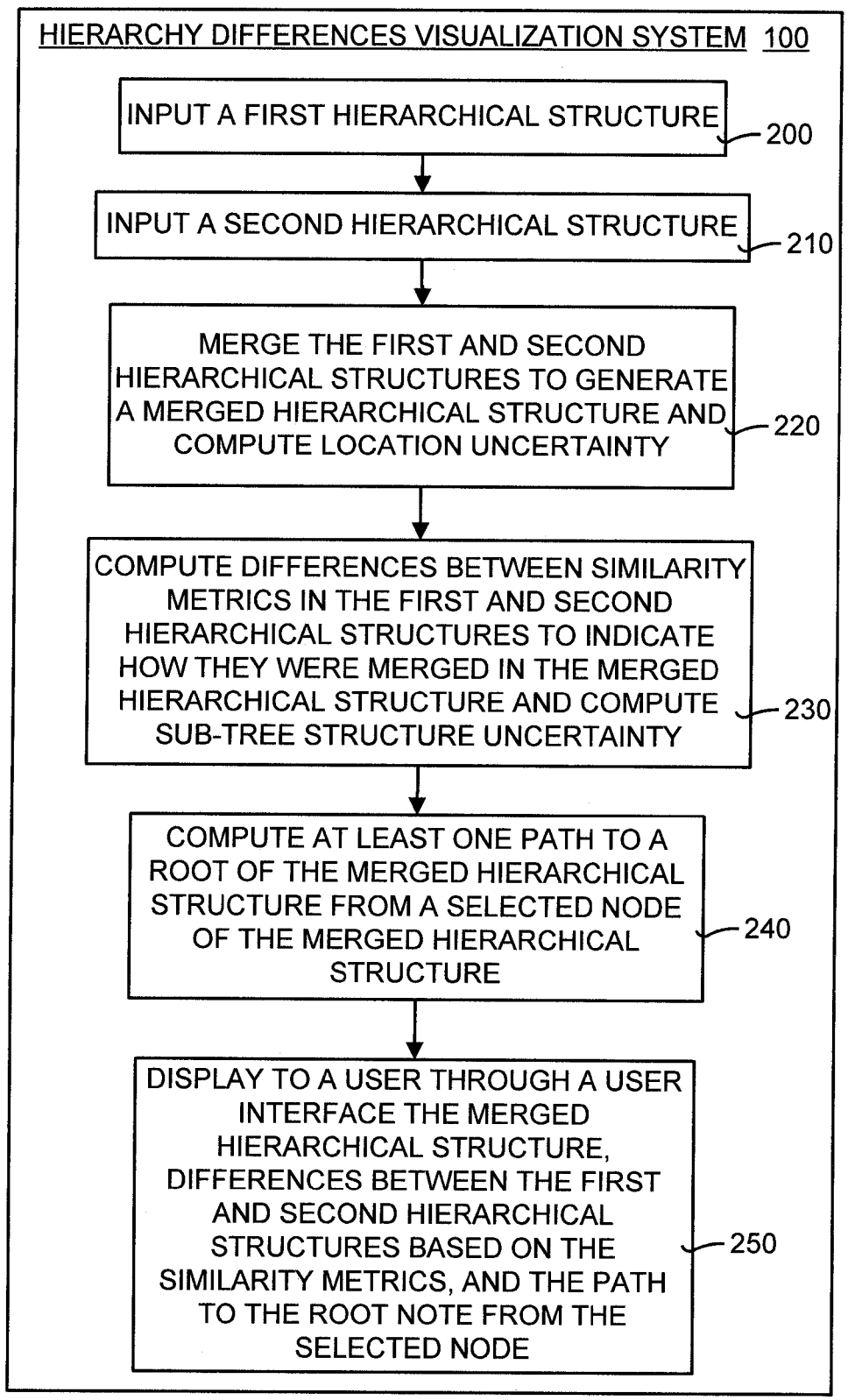
FIG. 2 is a block diagram illustrating the general overview of the operation of the method the hierarchy differences visualization system shown in FIG. 1.

FIG. 2 is a block diagram illustrating the general overview of the operation of the method the hierarchy differences visualization system 100 shown in FIG. 1. The method begins by inputting a first hierarchical structure (box 200) and a second hierarchical structure (box 210). Next, these two structures are merged to generate a merged hierarchical structure (box 220).

Uncertainty (or change) is found by computing differences between the two structures based on similarity metrics. For example, the similarity metric may be a structural metric such that the structural differences between the two structures are computed. These differences are used to indicate how the two structures were merged into the merged hierarchical structure. In other words, any differences between the two structures based on the similarity metrics are shown in the merged hierarchical structure. One such structural similarity metric is a location uncertainty. The location uncertainty may be found during the merge process (box 220). Another Structural similarity metric is sub-tree structure uncertainty. The sub-tree structure uncertainty may be computed after the merge process (box 230).

At least one path to a root of the merged hierarchical structure is computed (box 240). This path is computed to the root from a selected node in the merged hierarchical structure. This node may be selected by a user through the hierarchy differences user interface 190, described in detail below. The user interface 190 then is used to display to a user the merged hierarchical structure, the differences between the two structures based on the similarity metrics, and the path to the root from a selected node (box 250).

II. Operational and System Details

The hierarchy differences visualization system and method displays the structural uncertainty of similar hierarchies. The system and method automatically merges two tree structures into a single tree structure and computes uncertainty based on the differences of similarity metrics between the two tree structures.

In order to describe the hierarchy differences visualization system and method in detail, tree structures containing a set of two classification of scientific names of birds are used. A first classification is from the National Center for Biotechnology Information (NCBI) and a second classification is from the Animal Diversity Web (ADW). The fact that these two authoritative sources disagree on these classifications illustrates the degree of uncertainty in biological classifications. This is an example of the type of uncertainties that the hierarchy differences visualization system and method helps expose.

Structural Uncertainty

In some embodiments of the hierarchy differences visualization system and method, one similarity metric used is structural uncertainty. However, it should be noted that other types of similarity metrics may be used in addition to or in place of this similarity metric. Structural uncertainty now will be discussed in further detail.

In situations where the correct tree structures are unknown, the differences between two tree structures are interpreted as structural uncertainty. For each node, two types of structural uncertainty may be measured: (1) location; and (2) sub-tree structure.

Location Uncertainty

Within a tree structure, the location of a node can be represented in two different ways: (1) an absolute path from the root; and (2) a relative path from its parent. The main drawback of the first representation is that a small difference close to the root affects its whole sub-tree. Therefore, the hierarchy differences visualization system and method uses the relative path to compute the uncertainty in node location. The location uncertainty is not scalar but is categorical in value. The three possible categories are as follows:

1. A node is in both trees at the same location (in other words, under same parent). This is the most certain case;
2. A node is in both trees but at different locations (in other words, under different parents);
3. A node is included in only one of the trees. This is the most uncertain case.

Sub-Tree Structure Uncertainty

Irrespective of whether a node is in the same location in two tree structures, its sub-tree structures can be different. The hierarchy differences visualization system and method computes the sub-tree structure uncertainty by measuring how many links overlap in two sub-trees. Thus, the sub-tree structure uncertainty function for a node v can be defined as follows:

$$\text{sub-tree structure uncertainty}(v) = 1 - \frac{n(L_1(v) \cap L_2(v))}{n(L_1(v) \cup L_2(v))},$$

where $L_i(v)$ is the set of links in the sub-tree of v in the $i^{th}$ tree.

Generating a Merged Tree Structure

Figure 3:
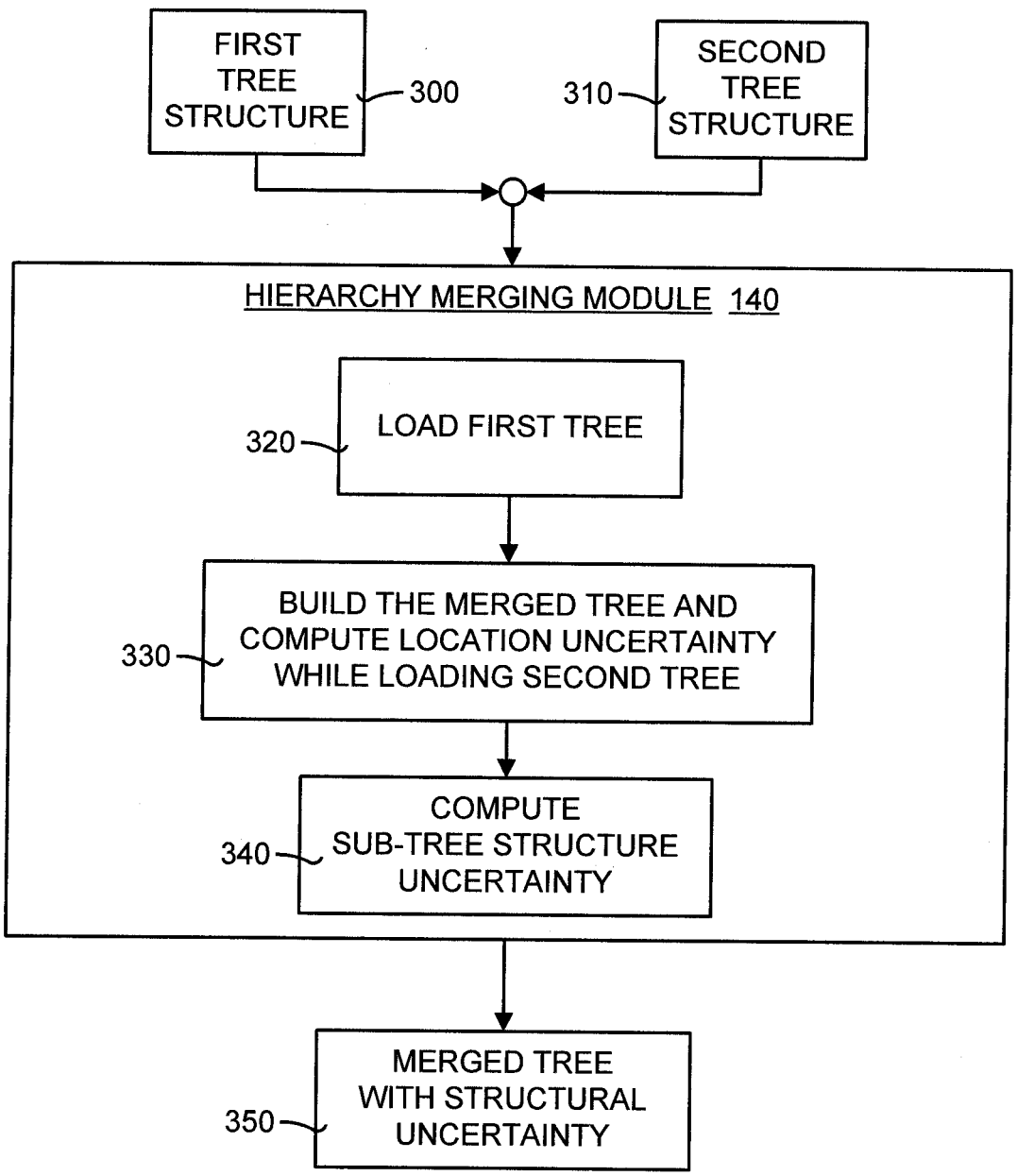
FIG. 3 is a flow diagram illustrating the operation of the hierarchy merging module shown in FIG. 1.

FIG. 3 is a flow diagram illustrating the operation of the hierarchy merging module 140 shown in FIG. 1. In this implementation of the hierarchy merging module 140, the hierarchical structures are tree structures. Moreover, the similarity metric used is structural uncertainty.

As shown in FIG. 3, a first tree structure 300 and a second tree structure 310 are input to the hierarchy merging module 140. The first tree structure is loaded first (box 320). Next, while loading the second tree structure, the module 140 simultaneously merges the second tree structure to the first tree structure and computes the location uncertainty (box 330). Once the merged tree is built, the module 140 computes sub-tree structure uncertainty (box 340). In some embodiments this is achieved by recursively counting the number of links in the sub-trees of the node. The output of the module 140 is a merged tree structure with structural uncertainty computed (box 350). In some embodiments, the hierarchy differences visualization system and method builds a merged tree structure and computes uncertainty at startup.

In some embodiments, each node in the merged tree structure is represented as a Hierarchy Differences Visualization object. The Hierarchy Differences Visualization class contains member variables for the tree structure such as parents and arrays of Hierarchy Differences Visualization children. It also contains to which tree structures the node belong. When a node is included in both trees under different nodes, the view nodes are duplicated, as represented by Hierarchy Differences Visualization instances. The Hierarchy Differences Visualization class contains an array of Hierarchy Differences Visualization instances, one for each view node. The Hierarchy Differences Visualization object contains the Hierarchy Differences Visualization instance as a data node. In addition to position information for layout, it also contains the tree structure information such as left (and right) sibling, left (and right) neighbor, parent, and so on. Since one data node can map to two view nodes, the view node object also contains to which tree it belongs.

Computing a Path in Tree Structures

Figure 4:
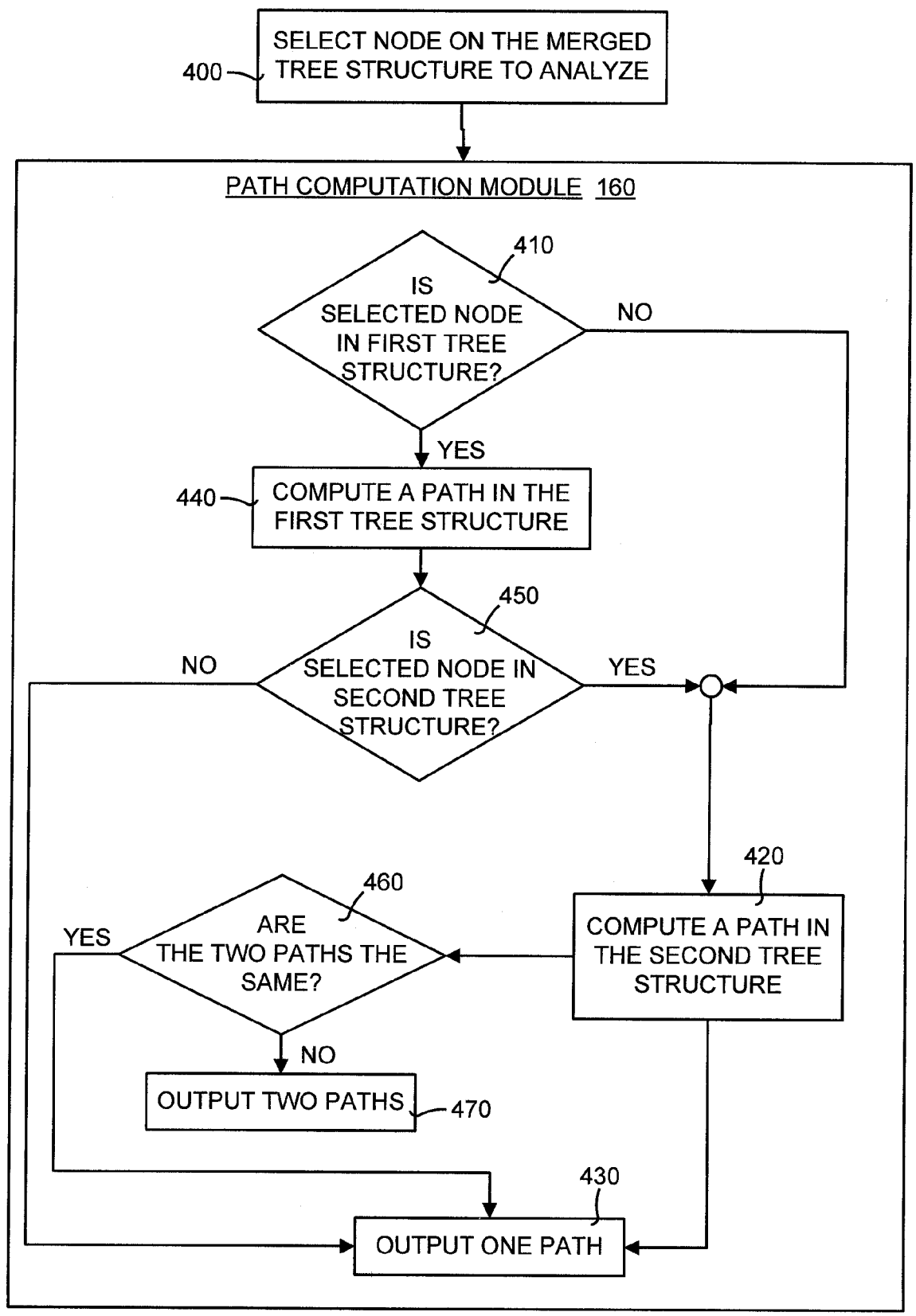
FIG. 4 is a flow diagram illustrating the operation of the path computation module shown in FIG. 1.

FIG. 4 is a flow diagram illustrating the operation of the path computation module 160 shown in FIG. 1. The module inputs a selected node on the merged tree structure to analyze (box 400). In some embodiments, a user selects a node from the merged tree structure.

Once a node is selected, the module 160 computes paths to the root of the merged tree structure from the selected node. Specifically, a determination is made as to whether the selected node is in the first tree structure (box 410). If not, then the module 160 assumes the node is in the second tree structure and computes a path in the second tree structure (box 420). The one path then is output (box 430). If so, then the module 160 computes a path in the first tree structure (box 440).

A determination then is made as to whether the selected node is in the second tree structure (box 450). If not, then the output is one path (box 430). If so, then the module 160 computes a path in the second tree structure (box 420). Next, a determination is made as to whether the two paths are the same (box 460). If they are the same, then the output is one path (box 430). Otherwise, if the two paths are not the same, then the output is two paths (box 470). The output of one path or two paths then is displayed in the paths view area of the hierarchy differences user interface 190, as discussed below.

Hierarchy Differences User Interface

The hierarchy differences visualization system and method includes the hierarchy differences user interface 190. Node visualization metrics are used in the user interface 190 to display differences between the first and second hierarchical structures based on the similarity metrics. In some embodiments, the first and second hierarchical structures are tree structures and the similarity metric is structural uncertainty.

Figure 5:
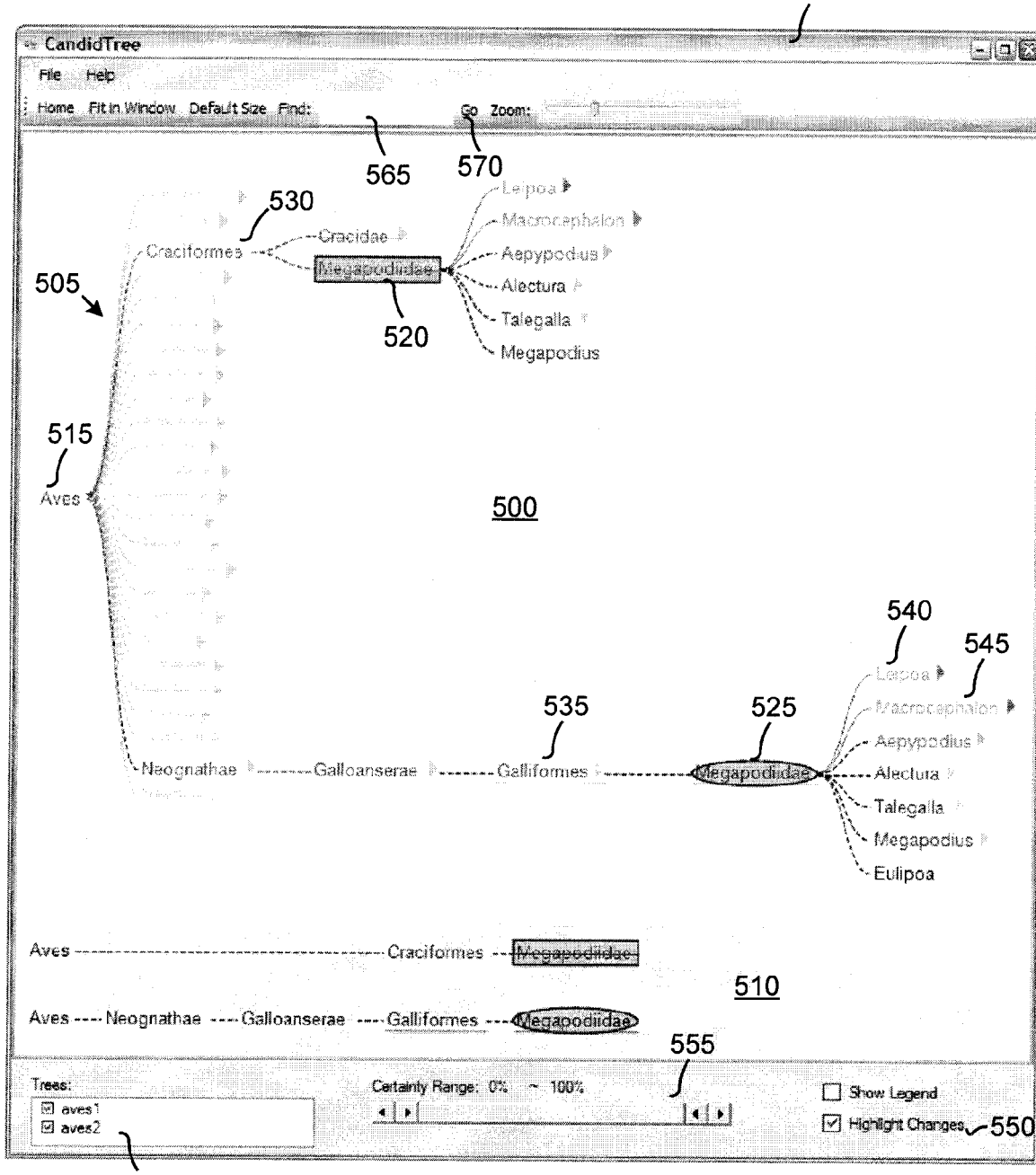
FIG. 5 is an exemplary embodiment of the hierarchy differences user interface 190 shown in FIG. 1.

FIG. 5 is an exemplary embodiment of the hierarchy differences user interface 190 shown in FIG. 1. In the embodiment shown in FIG. 5, the user interface 190 includes two views. A first view is a tree browser 500 that to display a merged tree structure 505. A second view is a paths view 510 that shows paths to the root 515 in each tree structure from the currently selected node 520 and a matching node 525.

Node visualization metrics used in the user interface 190 shown in FIG. 5 may take many forms, depending on the embodiment. These node visualization metrics include various node colors, shading, and transparency. In the following discussion of the user interface 190, specific colors are listed. However, it should be noted that alternate colors may be used and various colors may be used to indicate different things. The colors shown in FIG. 5 are simply one embodiment of the hierarchy differences user interface 190.

The hierarchy differences user interface 190 displays the location uncertainty of a node relative to its parent by a color of the node label. In some embodiments, the color transparent black or gray means that the node is included in both trees under the same node. For example, in FIG. 5, the labels of the upper six nodes to the right of the matching node 525 are grey and transparent black and the labels of the six nodes to the right of the currently selected node 520 are also grey and transparent black, indicating that these nodes are included in both the first tree structure and the second tree structure under the same parent.

In some embodiments, red indicated that a node has been deleted and blue indicates that a node has been added. Blue underline means that the node was moved from another location and added, while blue without underlining means that the node simply was added. For example, referring to FIG. 5, the colors red and blue indicate that a node is included in the first and second tree structures, respectively. If the node is included in both tree structures but under different nodes, this means that the node moved from the first tree structure to the second tree structure. In order to represent this move situation, the user interface 190 shows the red node in the first tree with a strikethrough and the blue node in the second tree with an underline. For example, as shown in FIG. 5, "Megapodiidae" (the second selected node 525) was under "Craciformes" 530 in the first tree structure and then moved under "Galliformes" 535 in the second tree structure.

The hierarchy differences user interface 190 also uses a metric to convey sub-tree structure uncertainty. In some embodiments, the sub-tree structure uncertainty of a node is shown by a transparency of a node label. In order to make the node readable even if uncertainty is very high, the user interface uses 128 as a minimum alpha value, which corresponds to 50% transparent. Note that it is difficult to distinguish small differences, such as the difference between 1 and 0.9. To help users distinguish the 100% certain information from less certain data, in some embodiments the user interface 190 uses a solid link only when the sub-tree structure uncertainty is 0.

By way of example, referring again to FIG. 5, among the children of "Megapodiidae" (the matching node 525), the sub-tree structure uncertainty of "Leipoa" 540 and "Macrocephalon" 545 is zero and that of the others is non-zero. Thus, these two nodes 540, 545 are transparent while the other nodes in the sub-tree structure are less transparent, indicating more certainty. To indicate uncertainty, these embodiments use four discrete alpha values: (1) 255 (0% transparent) when the uncertainty (u)=0; (2) 214 (=16% transparent) when $0.5 \leq u \leq 1$; (3) 171 (≈33% transparent) when $0 < u < 0.5$; and (4) 128 (50% transparent) when u=1. To enable users to compare uncertainties in the same range, the user interface 190 provides exact values in a tooltip (not shown). The default set of alpha values means that the more certain the data, the more opaque (and readable) is the data. However, users may want to focus on uncertain (different) information depending on data and tasks. The user interface 190 reverses the order of alpha values when users check the "Highlight Changes" check box 550, shown in FIG. 5 in the bottom right. This makes uncertain information more readable.

Children of each node are grouped by location uncertainty. This location uncertainty includes: (1) nodes only in the first tree; (2) nodes moved from first tree; (3) nodes in both trees; (4) nodes moved to the second tree; and (5) nodes only in the second tree. This helps a user capture only one tree from the merged tree. For example, if users want to focus on the first tree, they can ignore groups (4) and (5). Within each group, by default, children are sorted by sub-tree structure uncertainty.

Changes in Paths to the Root

When a user clicks on a moved node in the tree browser 500, which is either red with strikethrough or blue with underline, the hierarchy differences visualization system and method finds the matching node in the other tree and opens them together. The currently selected node 520 is indicated by a light blue background with a rectangular border and the matching node 525 is indicated by an oval border with a light blue background. In the exemplary example of FIG. 5, once a user clicks on "Megapodiidae" (the currently selected node 520) under "Craciformes" 530, then "Megapodiidae" (the matching node 525) under "Galliformes" 535 is automatically opened.

The tree browser 500 and paths view 510 of the user interface 190 are tightly coupled. For example, when a user selects a node in the tree browser 500, paths to the root 515 in both tree structures from the selected node 520 are shown in the paths view 510. As explained above in reference to the path computation module 160, if the selected node 520 is included in only one tree structure or its absolute location is the same in both tree structures, then only one path is shown. When two paths are different, then the user interface 190 vertically aligns the nodes with similar labels from two paths. In some embodiments the similarity of the labels is computed by a Levenshtein distance. This helps a user to see what changes have been made between two tree structures. The Levenshtein distance, which is well known in the art, is the minimum number of deletions, insertions, or substitutions required to transform one string into another. Spell checkers use this distance metric to find correct words similar to a misspelled word.

By way of example, FIG. 6 is an example illustrating of visualizing the path computation of two paths to a root 600 in a first tree structure 610 and a second tree structure 620. Specifically, two levels, namely "Neognathae" 630 and "Neoaves" 640, are added to the second tree structure 620 between "Aves" 600 and "Strigiformes" 650. It should be noted that "Strigiformes" in the first tree structure 610 is a selected node because its label has a blue background with a rectangular border, and "Strigiformes" in the second tree structure 620 is a matching node because its label has blue background with an oval border.

Path computation can also help a user identify possible errors in node labels. FIG. 7 is an example of node alignment with similar labels from two paths. The first path is from a first tree structure 700 and the second path is from a second tree structure 710. Note in the second tree structure 710, the parent of "Musophagidae" 720 is spelled "Musphagiformes" 730 but in reality is supposed to be spelled "Musophagiformes" 740 as in the first tree structure. Thus, "Musphagiformes" in the second tree structure 710 is a typographical error. When a user clicks on a node in the paths view 510, the hierarchy differences visualization system and method temporarily highlights the corresponding node in the tree browser 500 with a thick purple rectangle (not shown) surrounding the node so that the user can recognize the location of the node. In addition, if the corresponding node is off-screen, the hierarchy differences visualization system and method pans over on the merged tree structure 505 to allow viewing of the node. In FIG. 7 even though the term is misspelled, the system and method aligned "Musophagiformes" 740 with "Musphagiformes" 730 because it is the most similar node from among the nodes in the second tree structure 710.

Emphasizing Nodes of Interest and Search

As a user browses through the merged tree structure 505, especially for a structure with large fan outs, the selected node and its matching node could be very far away from each other and the matching node could be off-screen. Even when there is no matching node, the screen may be still cluttered. It is assumed that a user is mainly interested in the selected node and its children, siblings, and ancestors. In some embodiments, when a user selects a node, the hierarchy differences visualization system and method uses a fisheye technique and deemphasizes all other nodes by making them smaller and less opaque. This is shown in FIG. 5, such that nodes to the left of the currently selected node 520 are deemphasized and smaller and less opaque. Moreover, the same technique is applied to the matching node 525.

For the case where a user is only interested in the nodes with a specific certainty range, the hierarchy difference user interface 190 provides a double-headed range bar 555 in the control panel to allow users to unhighlight nodes that do not meet the certainty requirement. This is shown at the bottom center of FIG. 5. A user can focus on one tree by manipulating the checked boxes in the Trees list 560, shown at the left bottom of FIG. 5. The unchecked tree is unhighlighted. Since in some embodiments 128 (50% transparent) was used as an alpha value for the most uncertain nodes for readability, the user interface 190 uses an alpha value of 64 (75% transparent) for unhighlighted nodes.

Figure 8:
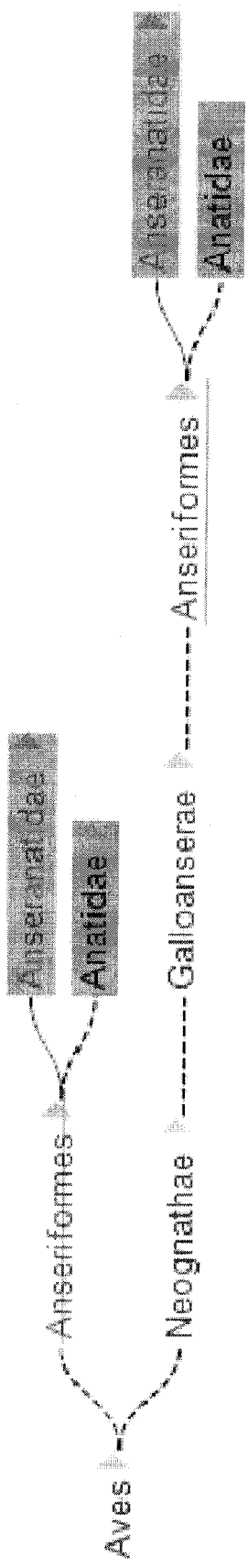
FIG. 8 is an example of a search performed in the hierarchy difference user interface.

Some embodiments of the hierarchy differences visualization system and method also provide support for searching, involving providing simple substring match with node labels. Referring to FIG. 5, typing a word in the text box 565 and pressing the "Go" button 570 displays the search results colored in orange and restricts the view to the nodes relevant to the search results. FIG. 8 is an example of a search performed in the hierarchy difference user interface 190. In particular, a search for "Anatidae" shows four search results (containing the keyword) and nodes relevant to the search results, with the search results highlighted in orange.

III. Exemplary Operating Environment

The hierarchy differences visualization system and method is designed to operate in a computing environment. The following discussion is intended to provide a brief, general description of a suitable computing environment in which the hierarchy differences visualization system and method may be implemented.

Figure 9:
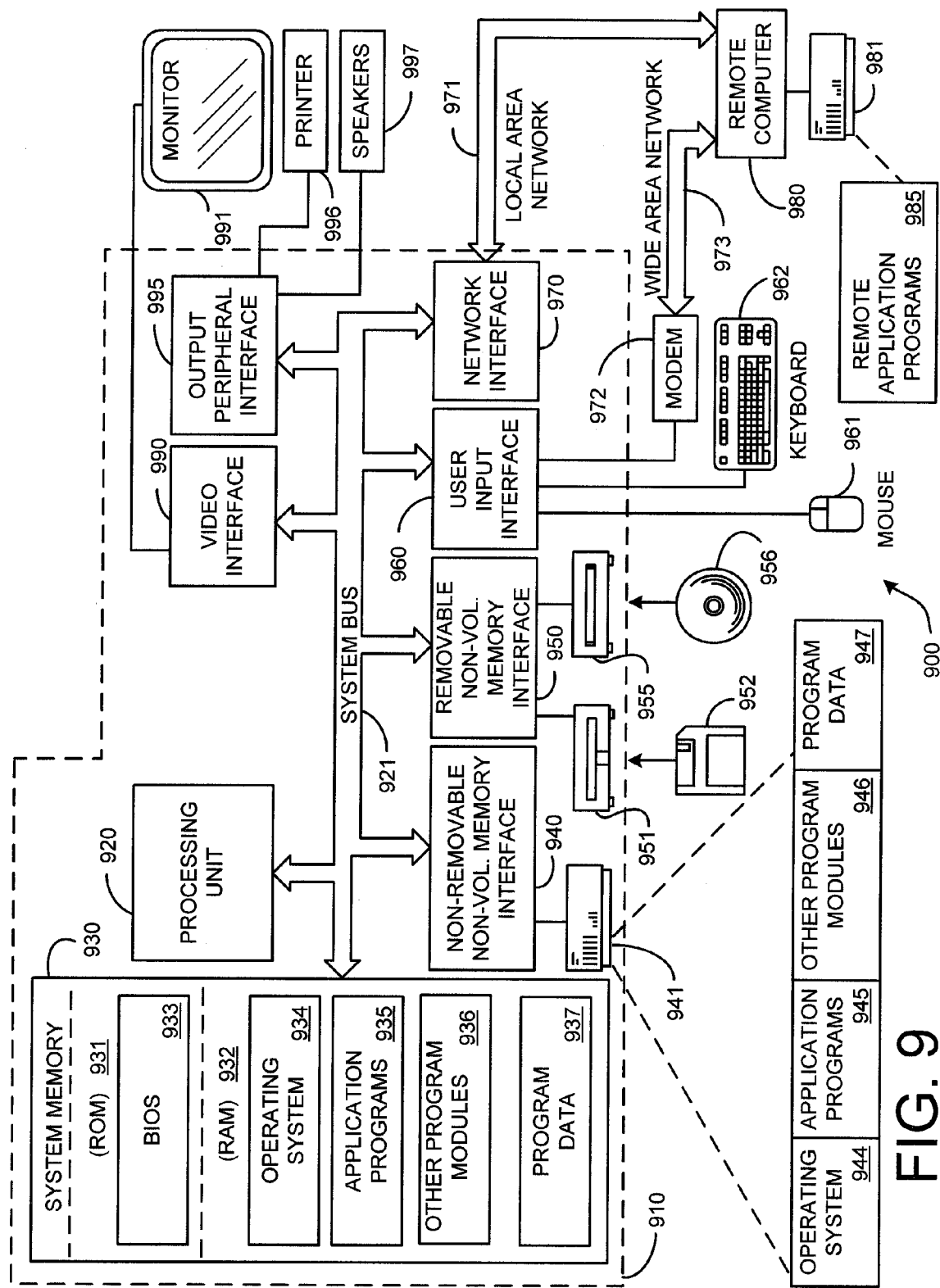
FIG. 9 illustrates an example of a suitable computing system environment in which the hierarchy differences visualization system and method may be implemented.

FIG. 9 illustrates an example of a suitable computing system environment in which the hierarchy differences visualization system and method may be implemented. The computing system environment 900 is only one example of a suitable computing environment and is not intended to suggest any limitation as to the scope of use or functionality of the invention. Neither should the computing environment 900 be interpreted as having any dependency or requirement relating to any one or combination of components illustrated in the exemplary operating environment.

The hierarchy differences visualization system and method is operational with numerous other general purpose or special purpose computing system environments or configurations. Examples of well known computing systems, environments, and/or configurations that may be suitable for use with the hierarchy differences visualization system and method include, but are not limited to, personal computers, server computers, hand-held (including smartphones), laptop or mobile computer or communications devices such as cell phones and PDA's, multiprocessor systems, microprocessor-based systems, set top boxes, programmable consumer electronics, network PCs, minicomputers, mainframe computers, distributed computing environments that include any of the above systems or devices, and the like.

The hierarchy differences visualization system and method may be described in the general context of computer-executable instructions, such as program modules, being executed by a computer. Generally, program modules include routines, programs, objects, components, data structures, etc., that perform particular tasks or implement particular abstract data types. The hierarchy differences visualization system and method may also be practiced in distributed computing environments where tasks are performed by remote processing devices that are linked through a communications network. In a distributed computing environment, program modules may be located in both local and remote computer storage media including memory storage devices. With reference to FIG. 9, an exemplary system for the hierarchy differences visualization system and method includes a general-purpose computing device in the form of a computer 910 (the computer 910 is one example of the computing device 110 shown in FIG. 1).

Components of the computer 910 may include, but are not limited to, a processing unit 920 (such as a central processing unit, CPU), a system memory 930, and a system bus 921 that couples various system components including the system memory to the processing unit 920. The system bus 921 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer 910 typically includes a variety of computer readable media. Computer readable media can be any available media that can be accessed by the computer 910 and includes both volatile and nonvolatile media, removable and non-removable media. By way of example, and not limitation, computer readable media may comprise computer storage media and communication media. Computer storage media includes volatile and nonvolatile removable and non-removable media implemented in any method or technology for storage of information such as computer readable instructions, data structures, program modules or other data.

Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the computer 910. Communication media typically embodies computer readable instructions, data structures, program modules or other data in a modulated data signal such as a carrier wave or other transport mechanism and includes any information delivery media.

Note that the term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

The system memory 940 includes computer storage media in the form of volatile and/or nonvolatile memory such as read only memory (ROM) 931 and random access memory (RAM) 932. A basic input/output system 933 (BIOS), containing the basic routines that help to transfer information between elements within the computer 910, such as during start-up, is typically stored in ROM 931. RAM 932 typically contains data and/or program modules that are immediately accessible to and/or presently being operated on by processing unit 920. By way of example, and not limitation, FIG. 9 illustrates operating system 934, application programs 935, other program modules 936, and program data 937.

The computer 910 may also include other removable/non-removable, volatile/nonvolatile computer storage media. By way of example only, FIG. 9 illustrates a hard disk drive 941 that reads from or writes to non-removable, nonvolatile magnetic media, a magnetic disk drive 951 that reads from or writes to a removable, nonvolatile magnetic disk 952, and an optical disk drive 955 that reads from or writes to a removable, nonvolatile optical disk 456 such as a CD ROM or other optical media.

Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 941 is typically connected to the system bus 921 through a non-removable memory interface such as interface 940, and magnetic disk drive 951 and optical disk drive 955 are typically connected to the system bus 921 by a removable memory interface, such as interface 950.

The drives and their associated computer storage media discussed above and illustrated in FIG. 9, provide storage of computer readable instructions, data structures, program modules and other data for the computer 910. In FIG. 9, for example, hard disk drive 941 is illustrated as storing operating system 944, application programs 945, other program modules 946, and program data 947. Note that these components can either be the same as or different from operating system 934, application programs 935, other program modules 936, and program data 937. Operating system 944, application programs 945, other program modules 946, and program data 947 are given different numbers here to illustrate that, at a minimum, they are different copies. A user may enter commands and information (or data) into the computer 910 through input devices such as a keyboard 962, pointing device 961, commonly referred to as a mouse, trackball or touch pad, and a touch panel or touch screen (not shown).

Other input devices (not shown) may include a microphone, joystick, game pad, satellite dish, scanner, radio receiver, or a television or broadcast video receiver, or the like. These and other input devices are often connected to the processing unit 920 through a user input interface 960 that is coupled to the system bus 921, but may be connected by other interface and bus structures, such as, for example, a parallel port, game port or a universal serial bus (USB). A monitor 991 or other type of display device is also connected to the system bus 921 via an interface, such as a video interface 990. In addition to the monitor, computers may also include other peripheral output devices such as speakers 997 and printer 996, which may be connected through an output peripheral interface 995.

The computer 910 may operate in a networked environment using logical connections to one or more remote computers, such as a remote computer 980. The remote computer 980 may be a personal computer, a server, a router, a network PC, a peer device or other common network node, and typically includes many or all of the elements described above relative to the computer 910, although only a memory storage device 981 has been illustrated in FIG. 9. The logical connections depicted in FIG. 9 include a local area network (LAN) 971 and a wide area network (WAN) 973, but may also include other networks. Such networking environments are commonplace in offices, enterprise-wide computer networks, intranets and the Internet.

When used in a LAN networking environment, the computer 910 is connected to the LAN 971 through a network interface or adapter 970. When used in a WAN networking environment, the computer 910 typically includes a modem 972 or other means for establishing communications over the WAN 973, such as the Internet. The modem 972, which may be internal or external, may be connected to the system bus 921 via the user input interface 960, or other appropriate mechanism. In a networked environment, program modules depicted relative to the computer 910, or portions thereof, may be stored in the remote memory storage device. By way of example, and not limitation, FIG. 9 illustrates remote application programs 985 as residing on memory device 981. It will be appreciated that the network connections shown are exemplary and other means of establishing a communications link between the computers may be used.

The foregoing Detailed Description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A computer-implemented method comprising:
using a computer to perform the following:
obtaining a first hierarchical structure having a plurality of first nodes;
obtaining a second hierarchical structure having a plurality of second nodes;
merging the first hierarchical structure and the second hierarchical structure to obtain a merged hierarchical structure having a plurality of third nodes corresponding to at least some of the plurality of first nodes and at least some of the plurality of second nodes;
determining a first path from a selected first node in the first hierarchical structure to a root of the merged hierarchical structure, wherein the selected first node corresponds to a selected third node and the first path comprises first path nodes from the plurality of first nodes;
determining a second path from a selected second node in the second hierarchical structure to the root, wherein the selected second node corresponds to the selected third node, the second path is different than the first path, and the second path comprises second path nodes from the plurality of second nodes;
computing distances between first labels of the first path nodes in the first path and second labels of the second path nodes in the second path to identify pairs of corresponding first path nodes and second path nodes with similar labels, the distances being computed based on numbers of deletions, insertions, or substitutions for transforming the first labels into the second labels; and
displaying a user interface comprising:
at least part of the merged hierarchical structure,
one or more differences between the first hierarchical structure and the second hierarchical structure,
the first path including the first path nodes, and
the second path including the second path nodes,
wherein the first path and the second path are displayed such that the pairs of corresponding first path nodes and second path nodes with similar labels are aligned on the user interface.

2. The computer-implemented method of claim 1, further comprising:
computing a sub-tree structure uncertainty of an individual third node in the merged hierarchical structure, the individual third node having a corresponding individual first node in the first hierarchical structure and a corresponding individual second node in the second hierarchical structure; and
depicting the sub-tree structure uncertainty of the individual third node on the user interface,
wherein computing the sub-tree structure uncertainty further comprises measuring a number of overlapping links in a first sub-tree of the corresponding individual first node in the first hierarchical structure and a second sub-tree of the corresponding individual second node in the second hierarchical structure.

3. The computer-implemented method of claim 2, further comprising:
defining a sub-tree structure uncertainty function for the individual third node as follows:

$$\text{sub-tree structure uncertainty}(v) = 1 - \frac{n(L_1(v) \cap L_2(v))}{n(L_1(v) \cup L_2(v))},$$

where v is the individual third node and $L_i(v)$ is a set of links in a sub-tree structure of v in an $i^{th}$ tree; and
computing the sub-tree structure uncertainty using the sub-tree structure uncertainty function.

4. The computer-implemented method of claim 1, further comprising:
receiving a user selection of the selected third node in the merged hierarchical structure; and
determining the first path, determining the second path, computing the distances, and aligning the pairs responsive to receiving the user selection.

5. The computer-implemented method of claim 1, wherein the Distances are Levenshtein distances.

6. The method of claim 1, wherein the pairs of corresponding first path nodes and second path nodes with similar labels are aligned vertically on the user interface.

7. One or more computer storage media comprising computer-readable instructions which, when executed by one or more processing units, cause the one or more processing units to perform acts comprising:
obtaining a first hierarchical structure having a plurality of first nodes;
obtaining a second hierarchical structure having a plurality of second nodes;
merging the first hierarchical structure and the second hierarchical structure to obtain a merged hierarchical structure having a plurality of third nodes corresponding to at least some of the plurality of first nodes and at least some of the plurality of second nodes;
receiving a user input identifying a selected third node of the hierarchical structure, the selected third node having a corresponding selected first node in the first hierarchical structure and a corresponding selected second node in the second hierarchical structure;
determining a first path from the selected first node in the first hierarchical structure to a root of the merged hierarchical structure, wherein the first path comprises first path nodes from the plurality of first nodes;
determining a second path from the selected second node in the second hierarchical structure to the root, wherein the second path is different than the first path and the second path comprises second path nodes from the plurality of second nodes;
computing distances between first labels of the first path nodes in the first path and second labels of the second path nodes in the second path to identify pairs of corresponding first path nodes and second path nodes with similar labels, the distances being computed based on numbers of deletions, insertions, or substitutions sufficient to transform the first labels into the second labels; and
displaying a user interface comprising:
at least part of the merged hierarchical structure,
one or more differences between the first hierarchical structure and the second hierarchical structure, the first path including the first path nodes, and the second path including the second path nodes, wherein the first path and the second path are displayed such that the pairs of corresponding first path nodes and second path nodes with similar labels are aligned on the user interface.

8. The one or more computer storage media of claim 7, the acts further comprising:

computing a sub-tree structure uncertainty of an individual third node in the merged hierarchical structure, the individual third node having a corresponding individual first node in the first hierarchical structure and a corresponding individual second node in the second hierarchical structure; and depicting the sub-tree structure uncertainty of the individual third node on the user interface.

9. The one or more computer storage media of claim 8, wherein the sub-tree structure uncertainty is depicted by displaying a corresponding node label of the individual third node with a level of transparency representing the sub-tree structure uncertainty.

10. The one or more computer storage media of claim 9, the acts further comprising:

computing the sub-tree structure uncertainty by measuring a number of overlapping links in a first sub-tree of the corresponding individual first node in the first hierarchical structure and a second sub-tree of the corresponding individual second node in the second hierarchical structure.

11. The one or more computer storage media of claim 7, wherein the first path is displayed separately from and not connected to the displayed at least part of the merged hierarchical structure.

12. The one or more computer storage media of claim 11, wherein the second path is displayed:

separately from and not connected to the at least part of the merged hierarchical structure, and separately from and not connected to the first path.

13. The one or more computer storage media of claim 12, wherein the first path is displayed with only the first path nodes connected and the second path is displayed with only the second path nodes connected.

14. The one or more computer storage media of claim 7, wherein the corresponding first path nodes and second path nodes with similar labels are aligned vertically on the user interface.

15. A system comprising:

a processing unit; and computer-readable instructions that, when executed by the processing unit, cause the processing unit to:

obtain a first hierarchical structure having a plurality of first nodes, obtain a second hierarchical structure having a plurality of second nodes, merge the first hierarchical structure and the second hierarchical structure to obtain a merged hierarchical structure having a plurality of third nodes corresponding to at least some of the plurality of first nodes and at least some of the plurality of second nodes, receiving a user input identifying a selected third node of the hierarchical structure, the selected third node having a corresponding selected first node in the first hierarchical structure and a corresponding selected second node in the second hierarchical structure;

determine a first path from the selected first node in the first hierarchical structure to a root of the merged hierarchical structure, wherein the first path comprises first path nodes from the plurality of first nodes;

determine a second path from the selected second node in the second hierarchical structure to the root, wherein the second path is different than the first path and the second path comprises second path nodes from the plurality of second nodes;

compute distances between first labels of the first path nodes in the first path and second labels of the second path nodes in the second path to identify pairs of corresponding first path nodes and second path nodes with similar labels, the distances being computed based on numbers of deletions, insertions, or substitutions used to transform the first labels into the second labels; and display a user interface comprising:

at least part of the merged hierarchical structure, the first path including the first path nodes, and the second path including the second path nodes, wherein the first path and the second path are displayed such that the pairs of corresponding first path nodes and second path nodes with similar labels are aligned on the user interface.

16. The system of claim 15, wherein the computer-readable instructions further cause the processing unit to:

display a corresponding label of another individual third node with a visual characteristic that indicates the another individual third node is included in both the first hierarchical structure and the second hierarchical structure under a common parent node.

17. The system of claim 16, wherein the visual characteristic is a color of the corresponding label.

18. The system of claim 17, wherein the computer-readable instructions further cause the processing unit to:

display a further label of a further individual third node in a second color that indicates the further individual third node does not have a common parent node in the first hierarchical structure and the second hierarchical structure.

19. The system of claim 15, wherein the first path is displayed separately from and not connected to the displayed at least part of the merged hierarchical structure.

20. The system of claim 19, wherein the second path is displayed:

separately from and not connected to the at least part of the merged hierarchical structure, and separately from and not connected to the first path.

* * * * *